(12) United States Patent
Carroux

(10) Patent No.: US 9,320,508 B2
(45) Date of Patent: Apr. 26, 2016

(54) EXPANDABLE MEDICAL ACCESS SHEATH

(71) Applicant: Gyrus ACMI, Inc., Southborough, MA (US)

(72) Inventor: Alexander Carroux, Waltham, MA (US)

(73) Assignee: Gyrus ACMI, Inc., Southborough, MA (US)

(*) Notice: Subject to any disclaimer, the term of this patent is extended or adjusted under 35 U.S.C. 154(b) by 101 days.

(21) Appl. No.: 14/191,668

(22) Filed: Feb. 27, 2014

(65) Prior Publication Data

US 2015/0238178 A1  Aug. 27, 2015

(51) Int. Cl.

| A61B 1/32 | (2006.01) |
|---|---|
| A61B 17/02 | (2006.01) |
| A61B 1/00 | (2006.01) |
| A61M 25/00 | (2006.01) |
| A61M 25/06 | (2006.01) |
| A61B 1/307 | (2006.01) |
| A61B 17/34 | (2006.01) |
| A61B 17/00 | (2006.01) |

(52) U.S. Cl.
CPC .......... *A61B 17/0218* (2013.01); *A61B 1/00154* (2013.01); *A61B 1/307* (2013.01); *A61M 25/0023* (2013.01); *A61M 25/0662* (2013.01); *A61B 17/3439* (2013.01); *A61B 2017/00867* (2013.01); *A61B 2017/0225* (2013.01); *A61B 2017/345* (2013.01); *A61M 2025/0024* (2013.01)

(58) Field of Classification Search
CPC .............. A61M 25/0013; A61M 25/0017; A61M 2025/0681; A61M 29/00; A61B 17/3417; A61B 17/3431
See application file for complete search history.

(56) References Cited

U.S. PATENT DOCUMENTS

| 4,738,666 A | 4/1988 | Fuqua ........................ 604/280 |
|---|---|---|
| 6,231,598 B1 | 5/2001 | Berry et al. .................. 623/1.15 |
| 6,471,684 B2 | 10/2002 | Dulak et al. .................. 604/523 |
| 6,589,212 B1 | 7/2003 | Navis ....................... 604/164.01 |
| 7,654,989 B2 | 2/2010 | Knapp ........................ 604/284 |
| 7,776,062 B2 * | 8/2010 | Besselink et al. ............. 606/191 |
| 8,728,153 B2 * | 5/2014 | Bishop et al. ................ 623/2.11 |
| 2003/0220683 A1 | 11/2003 | Minasian et al. ............ 623/1.15 |

(Continued)

FOREIGN PATENT DOCUMENTS

| CN | 2792524 Y | 7/2006 |
|---|---|---|
| EP | 2 179 762 A1 | 4/2010 |
| EP | 2 374 402 A1 | 10/2011 |
| EP | 2 374 403 A1 | 10/2011 |
| EP | 1 441 636 B1 | 1/2012 |

*Primary Examiner* — Anu Ramana
(74) *Attorney, Agent, or Firm* — Harrington & Smith

(57) ABSTRACT

A medical access sheath including a first member, a second member and a third member. The first member includes a longitudinal length and a channel therethrough. The first member includes a slit along the longitudinal length. The channel is configured to expand from a first cross-sectional size to a larger second cross-sectional size. The slit is configured to enlarge as the channel expands. The second member is connected to the first member proximate the slit. The second member extends across the slit. The second member is configured to expand from first configuration to second configuration. The third member is removably located within the channel. The third member is configured to keep the second member in the first configuration when the third member is located in the channel. The third member is configured to release the second member to the second configuration when the third member is removed from the channel.

9 Claims, 4 Drawing Sheets

(56) References Cited

U.S. PATENT DOCUMENTS

| | | | |
|---|---|---|---|
| 2008/0033244 A1 | 2/2008 | Matsui et al. | 600/114 |
| 2008/0200943 A1 | 8/2008 | Barker et al. | 606/192 |
| 2010/0241214 A1 | 9/2010 | Holzer et al. | 623/1.15 |
| 2011/0105984 A1* | 5/2011 | Patel | A61M 1/3653 604/6.16 |
| 2013/0261399 A1 | 10/2013 | Lenker et al. | 600/204 |
| 2013/0324972 A1 | 12/2013 | Faherty et al. | 604/525 |
| 2014/0012281 A1 | 1/2014 | Wang et al. | 606/108 |

\* cited by examiner

EXPANDABLE MEDICAL ACCESS SHEATH

BACKGROUND

1. Technical Field

The exemplary and non-limiting embodiments relate generally to a medical access sheath and, more particularly, to an access sheath configured to change size.

2. Brief Description of Prior Developments

A ureteral access sheath adapted for insertion into a urethra includes an elongate tubular member having a proximal end and a distal end. One type of known ureteral access sheath consist of stainless steel sheath surrounded by a polytatrafluoroethylene (PTFE) inner coating.

SUMMARY

The following summary is merely intended to be exemplary. The summary is not intended to limit the scope of the claims.

In accordance with one aspect, an example embodiment is provided in a medical access sheath comprising a first member comprising a longitudinal length and a channel therethrough, where the first member comprises a slit along the longitudinal length, where the channel is configured to expand from a first cross-sectional size to a larger second cross-sectional size, and where the slit is configured to enlarge as the channel expands; a second member connected to the first member proximate the slit, where the second member extends across the slit, and where the second member is configured to expand from a first configuration to the second configuration; and a third member removably located within the channel, wherein the third member is configured to keep the second member in the first configuration when the third member is located in the channel, and wherein the third member is configured to release the second member to the second configuration when the third member is removed from the channel.

In accordance with another aspect, an example embodiment is provided in a medical apparatus comprising a medical access sheath comprising a first member comprising a longitudinal length and a channel therethrough, where the first member comprises a slit along the longitudinal length, where the channel is configured to expand from a first cross-sectional size to a larger second cross-sectional size, and where the silt is configured to enlarge as the channel expands; and a second member connected to the first member proximate the slit, where the second member extends across the slit, and where the second member is configured to expand from a first configuration to a second configuration; and a dilator located in the channel, where the dilator comprises a receiving area along a longitudinal length of the dilator, where the receiving area comprises a portion of the second member located therein, and where the receiving area is configured to release the second member from a collapsed first configuration to an expanded second configuration as the dilator is slid out of the medical access sheath.

In accordance with another aspect, an example medical access sheath dilator is provided which is configured to be inserted through a channel of a medical access sheath, where the dilator comprises a receiving area along a longitudinal length of the dilator, where the receiving area is configured to have an expandable portion of the medical access sheath located therein, and where the receiving area is configured to release the expandable portion from a collapsed first configuration to an expanded second configuration as the dilator is slid out of the medical access sheath.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
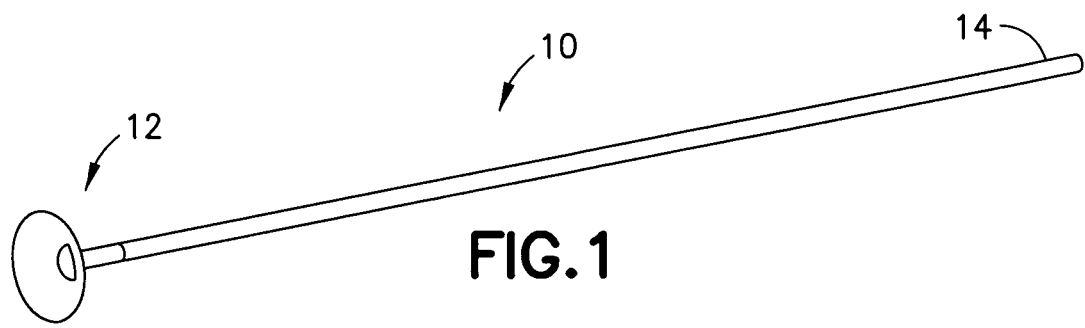
FIG. 1 is a perspective view of an example embodiment of a medical access sheath.

Referring to FIG. 1, there is shown a side perspective view of an apparatus 10 incorporating features of an example embodiment. Although the present invention will be described with reference to the embodiments shown in the drawings, it should be understood that the present invention can be embodied in many alternate forms of embodiments. In addition, any suitable size, shape or type of elements or materials could be used.

Figure 2:
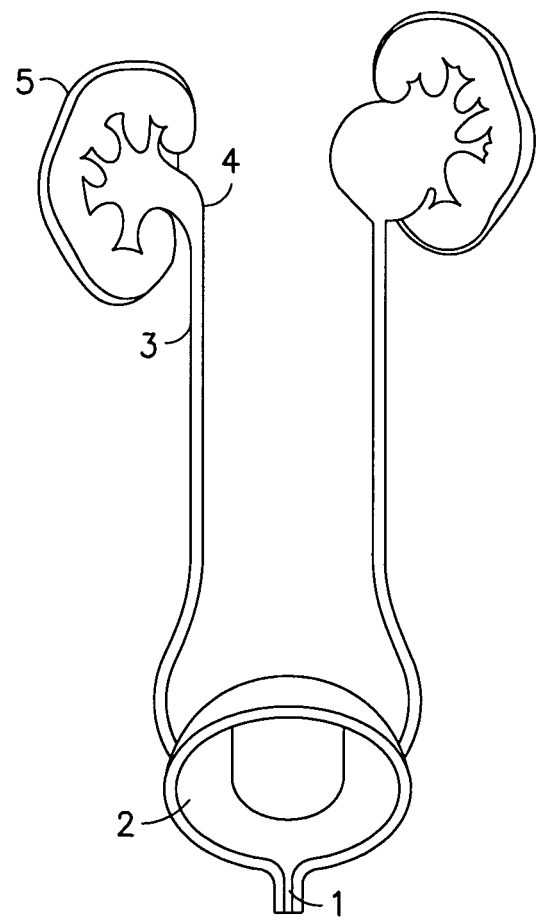
FIG. 2 is a diagram illustrating parts of a human body.
Figure 3:
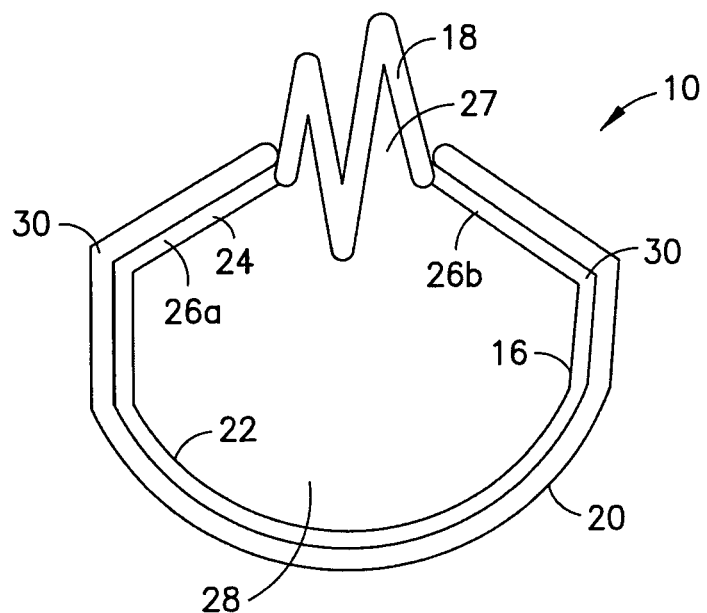
FIG. 3 is a schematic cross sectional view of the sheath shown in FIG. 1 in a collapsed configuration.

The apparatus 10 in this example embodiment is a medical, ureteral access sheath. Referring also to FIGS. 2-3, the access sheath 10 in this example is configured to extend through a patient's urethra 1, bladder 2 and ureter 3 and extend perhaps as far as the renal pelvis or ureteropelvic junction (UPJ) 4. The ureteropelvic junction (UPJ, also known as the ureteropelvic junction or ureteral pelvic junction) is the junction between the ureter and the renal pelvis of the kidney 5. Ureteral access sheaths provide a continuous working channel, simplifying areteroscopic procedures and protecting the ureter during multiple instrument exchanges. The sheath 10 is designed to facilitate ureteroscope insertion and re-insertion of instruments, such as an endoscope, allowing fragments of stones to be removed such as by a tool having a basket.

In this example the access sheath 10 comprises a flexible, elongated tubular shape having a proximal end 12 and a distal end 14. Referring also to FIG. 3, the sheath 10 has a first member 16, a second member 18 and a cover 20. In one type of example embodiment the sheath may comprise an inner liner on the interior facing surface of the first member 16, such as comprised of polytetrafluoroethylene (PTFE) for example.

The first member 16 forms a flexible, structural core for the sheath. In this example, the first member 16 has a general tube shape comprised of a shape memory alloy, such as NITINOL for example. The first member 16 is a one-piece member having a first section 22 and a second section 24. The first section 22 has a substantial semi-circular shape. The second section 24 has two movable flap portions 26a, 26b extending from opposite sides of the substantial semi-circular shape. The flap portions 26 are able to move relative to the first section 22 proximate the junctions 30. In alternate example embodiments, the shape of the first section 22 and/or the second section 24 may be different, and/or the second section 24 may comprise more or less than two flap portions. The first member 16 helps to form a working channel 28 for insertion of tools through the sheath, such as an endoscope for example. The core 16 may be lined with PTFE as an hydrophilic coating to reduce friction.

Figure 4:
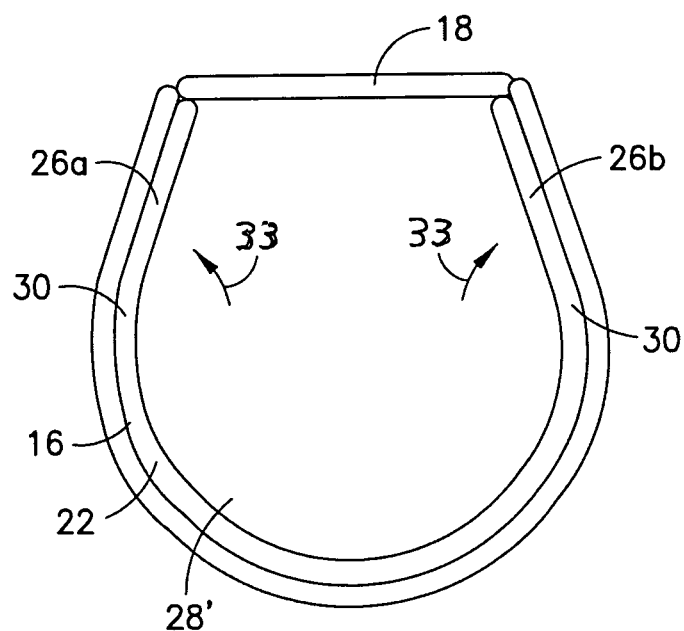
FIG. 4 is a schematic cross sectional view as in FIG. 3 of the sheath in an expanded configuration.

The second member 18 is a one-piece member comprised of a suitable material such as a plastic or polymer material. The second member 18 has a substantial foil shape which is connected to the two opposing flap portions 26 and covers the gap 27 between the opposing flap portions 26. The second member 18 is reconfigurable between a collapsed shape as shown in FIG. 3 and an expanded shape as shown in FIG. 4. In the collapsed shape the second member 18 is located, at least partially, inside the channel 28.

FIG. 3 shows the sheath in a natural, home configuration. FIG. 4 shows the sheath in an expanded configuration. In the expanded configuration the flap portions 26a, 26b have been deflected outward as indicated by arrows 33; bending at the junctions 30. The second member 18 is, thus, expanded between the enlarged gap between the ends of the flap portions 26. This enlarges the channel 28 into a new larger channel 28'.

Features as described herein may be used in an ureteral access sheath. With conventional access sheath technology, a physician has to select an access sheath size prior to the procedure. The size is selected depending on patient anatomy, scope size and the physician's preference to remove large stone fragments. Large access sheath are more traumatic to the ureter and sometimes it will be impossible to push the access sheath all the way up the UPJ (ureteropelvic junction). Features as described herein allow for a very slim sheath to be pushed up, but once in place a bigger lumen may be created, such as to allow for good fluid flow and large scopes/stones to be passed though the sheath. Features as described above allow for an access sheath with a flexible, NITINOL U-Shaped core, allowing for variable cross sectional area. Conventional access sheaths are based on a stainless-steel coil-reinforced sheath that prevents kinking, but does not allow for any flexibility in cross sectional area.

Figure 5:
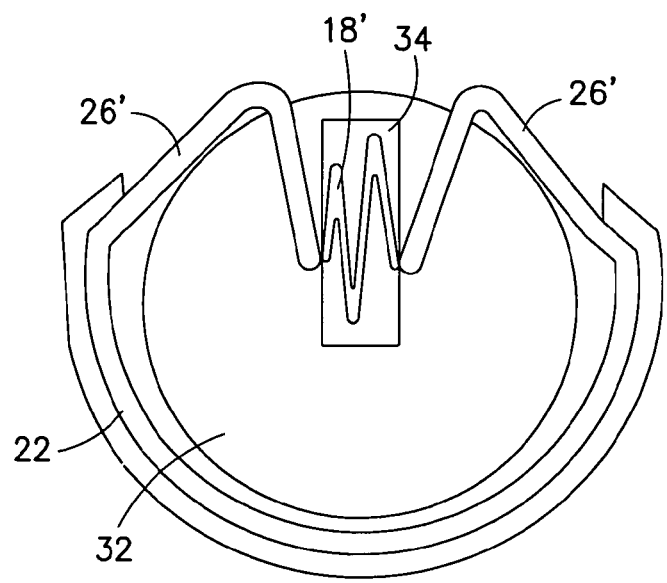
FIG. 5 is a schematic cross sectional view of another example embodiment shown with a dilator.
Figure 8:
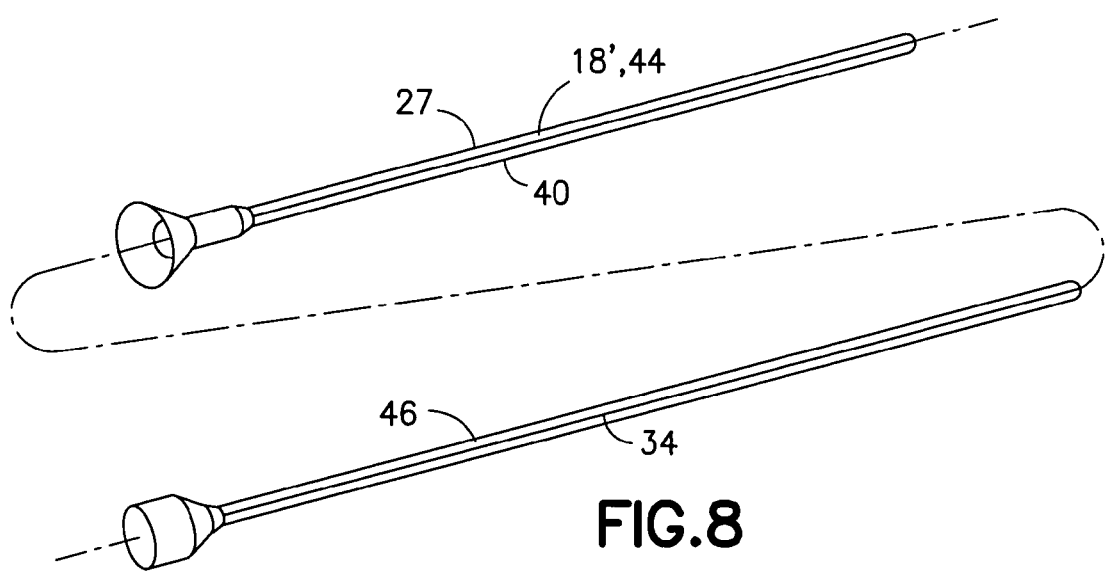
FIG. 8 is an exploded perspective view of the components shown in FIGS. 6 and 7.

The sheath can either be self-expending, based on a NITINOL spring action, or it may open when an instruments/irrigation are passed through. FIGS. 3-4 represent an embodiment where the sheath is expanded when an instruments/irrigation are passed through the channel 28. Referring also to FIG. 5, an embodiment is shown where a dilator 32 is used to control the sheath dimension. In this case, the dilator in the center would have a notch 34, with the second member 18' and at least part of the flap portions 26' being folded inside that notch 34. The access sheath may be loaded over a guidewire and pushed up the ureter. Once in place, the obturator may be removed and the sheath "flaps" would automatically unfold and open to a larger cross sectional area.

Features as described herein may provide a sheath comprising a slit or gap 27 and a foil 18 in the slit 27; the foil 18 configured to be folded. Features as described herein may provide a dilator configured to be inserted to the sheath and keep the foil folded. The foil may be unfolded by removing the dilator from the sheath. The sheath may be expanded by the unfolded foil. Unlike nephrostomy, where an artificial opening created between the kidney and the skin which allows for the urinary diversion directly from the upper part of the urinary system (renal pelvis), features as described herein may be used to extend an access sheath along the length of the ureter' perhaps up to the UPJ.

Figure 6:
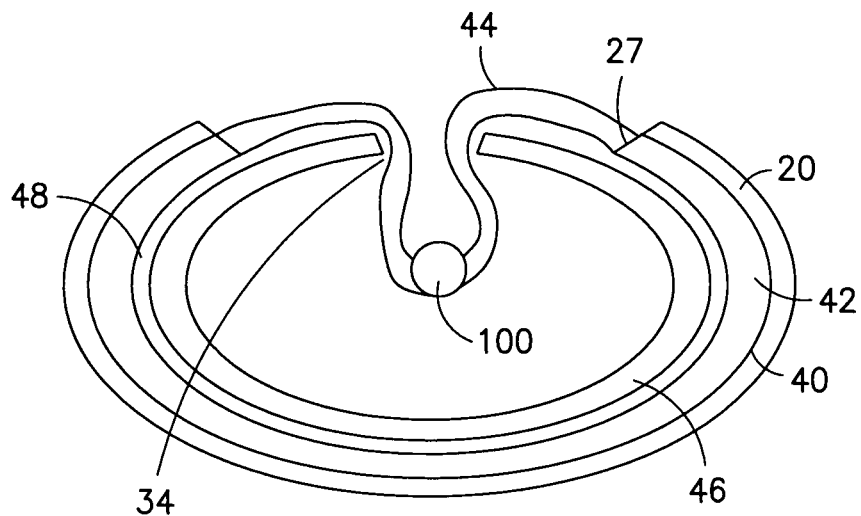
FIG. 6 is a schematic cross sectional view of another example embodiment shown with a dilator.
Figure 7:
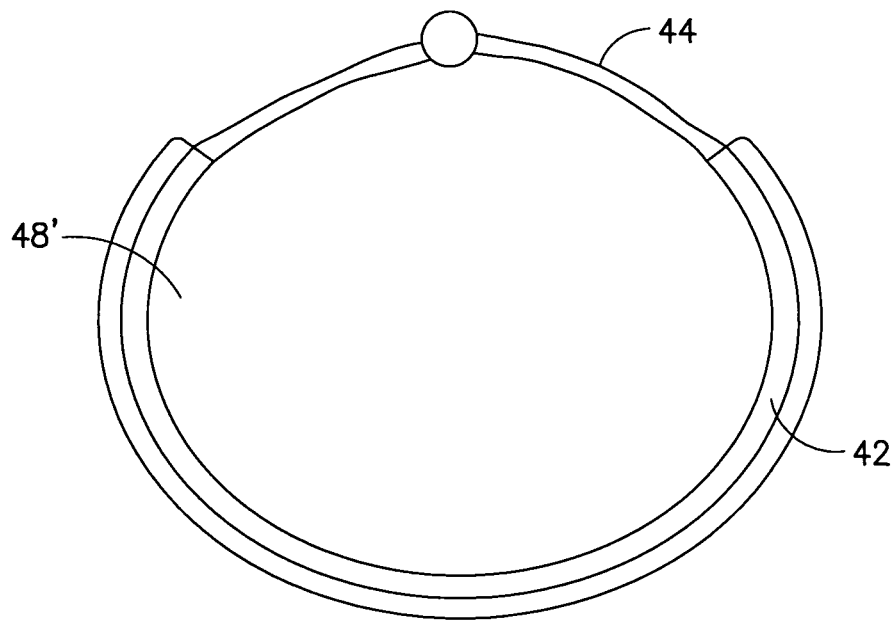
FIG. 7 is a schematic cross sectional view as in FIG. 6 with the dilator removed.

Referring also to FIGS. 6 and 7, another example is shown. FIG. 6 shows a sheath 40 having a core 42 made of shape memory alloy and a foil 44. The foil 44 may have a locking pars 100. A dilator 46 is provide to retain the foil 44 in its collapsed shape at least partially inside the core 42. The dilator 46 has a notch or groove along its length to retain the foil in its collapsed shape. The locking part 100 may help lock a portion of the foil 44 inside the dilator 46 until the dilator 46 is withdrawn. When the dilator 46 is removed as shown in FIG. 7, the spring properties of the core 42 automatically expand the shape of the channel 48 into 48', and the foil 44 unfolds and keeps the channel 48 substantially closed along the slit in the core 42.

In one example embodiment a medical access sheath comprises a first member having a longitudinal length and a channel therethrough, where the first member comprises a slit along the longitudinal length, where the channel is configured to expand from a first cross-sectional size to a larger second cross-sectional size, and where the slit is configured to enlarge as the channel expands; and a second member connected to the first member proximate the slit, where the second member extends across the slit, and where the second member is configured to expand when the channel expands from the first size to the second larger size.

The medical access sheath may further comprise a cover along the longitudinal length of the first member, where the cover is substantially not located on the second member. The medical access sheath may comprise a shape memory material, where the second member comprises a polymer material. The medical access sheath may comprise a foil, where the foil is substantially folded at the slit when the channel has the first cross-sectional size, and where the foil is substantially unfolded when the channel has the second cross-sectional size. The medical access sheath may have a home configuration with the channel having the second cross-sectional size, where the sheath is configured to automatically expand from a collapsed configuration, with the channel having the first cross-sectional size, to the home configuration with the channel having the second cross-sectional size. The medical access sheath may have a home configuration with the channel having the first cross-sectional size, where the sheath is configured to expand when an instrument is passed through the channel from the home configuration to an expanded configuration with the channel having the second cross-sectional size. When the medical access sheath is in a collapsed configuration with the channel having the first cross-sectional, size, at least a portion of the second member may be configured to be received in a receiving area of a dilator inserted into the channel. The first member may comprise a substantial semi-circular portion and two movable flap portions extending from opposite sides of the substantial semi-circular portion. An apparatus may be provided comprising the medical access sheath; and a dilator located in the channel, where the dilator comprises a receiving area along a longitudinal length of the dilator, where the receiving area has a portion of the second member located therein, and where the receiving area is configured to release the second member from a collapsed configuration to an expanded configuration as the dilator is slid out of the medical access sheath.

An example method may comprise changing a cross-sectional size of a channel in a tube of a medical access sheath from a first size to a different second size, where opposing ends of the tube along a longitudinal slit in the tube move relative to each other; and reconfiguring an expansion member, connected to the tube proximate the slit, to keep access to the channel through the slit closed as the size of the channel changes between the first and second sizes.

Changing of the cross sectional size may comprise removing a dilator from the channel. Changing of the cross sectional size may comprise inserting an instrument into the channel.

Changing of the cross sectional size may comprise the tube automatically springing from a first collapsed configuration to a second expanded configuration. The expansion member may comprise a foil, where the foil is substantially folded at the silt when the channel has the first cross-sectional size, and where the foil is substantially unfolded when the channel has the second cross-sectional size. The tube may comprise a substantial semi-circular portion and two movable flap portions extending from opposite sides of the substantial semi-circular portion, where the flap portions move relative to the substantial semi-circular portion as the cross sectional size of the channel changes. The tube may comprise a shape memory material and where the expansion member is a foil, where the shape memory material provides a spring bias of the medical access sheath towards the first size or, alternatively, towards the second size. The expansion member may be a foil, and the foil may provide a spring bias of the medical access sheath towards the first size or, alternatively, towards the second size.

Another example embodiment may comprise a medical access sheath dilator configured to be inserted through a channel of a medical access sheath, where the dilator comprises a receiving area along a longitudinal length of the dilator, where the receiving area is configured to have an expandable portion of the medical access sheath located therein, and where the receiving area is configured to release the expandable portion from a collapsed first configuration to an expanded second configuration as the dilator is slid out of the medical access sheath. An apparatus may comprise the medical access sheath dilator; and the medical access sheath connected to the dilator. The medical access sheath may comprise a first member having a longitudinal length and a channel therethrough, where the first member comprises a slit along the longitudinal length, where the channel is configured to expand from a first cross-sectional size to a larger second cross-sectional size, and where the slit is configured to enlarge as the channel expands, and where the expandable portion is connected to the first member proximate the slit, where the expandable portion extends across the slit, and where the expandable portion is configured to expand when the channel expands from the first size to the second larger size.

A method of manufacturing a medical ureteral access sheath comprising providing a first member, where the first member comprises a longitudinal length and a channel therethrough, where the first member comprises a slit along the longitudinal length, where the channel is configured to expand from a first cross-sectional size to a larger second cross-sectional size, and where the slit is configured to enlarge as the channel expands; and connecting a second member to the first member proximate the slit, where the second member extends across the slit, and where the second member is configured to expand when the channel expands from the first size to the second larger size.

An example medical access sheath may comprise a first member comprising a longitudinal length and a channel therethrough, where the first member comprises a slit along the longitudinal length, where the channel is configured to expand from a first cross-sectional size to a larger second cross-sectional size, and where the slit is configured to enlarge as the channel expands; a second member connected to the first member proximate the slit, where the second member extends across the slit, and where the second member is configured to expand from a first configuration to the second configuration; and a third member removably located within the channel, wherein the third member is configured to keep the second member in the first configuration when the third member is located in the channel, and wherein the third member is configured to release the second member to the second configuration when the third member is removed from the channel.

An example medical apparatus may comprise a medical access sheath comprising a first member comprising a longitudinal length and a channel therethrough, where the first member comprises a slit along the longitudinal length, where the channel is configured to expand from a first cross-sectional size to a larger second cross-sectional size, and where the slit is configured to enlarge as the channel expands; and a second member connected to the first member proximate the slit, where the second member extends across the slit, and where the second member is configured to expand from a first configuration to a second configuration; and a dilator located in the channel, where the dilator comprises a receiving area along a longitudinal length of the dilator, where the receiving area comprises a portion of the second member located therein, and where the receiving area is configured to release the second member from a collapsed first configuration to an expanded second configuration as the dilator is slid out of the medical access sheath.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A medical access sheath assembly comprising:
   a first member comprising a length with a channel therethrough, where the first member comprises a wall having a gap through the wall, where the channel is configured to expand from a first cross-sectional size to a larger second cross-sectional size, and where the gap is configured to enlarge as the channel expands;
   a second member connected to the first member, where the second member extends across the gap, and where the second member is configured to expand from a first configuration to a second configuration; and
   a third member removably located within the channel, wherein the third member is configured to keep the second member in the first configuration when the third member is located in the channel, and wherein the third member is configured to release the second member to the second configuration when the third member is removed from the channel.

2. A medical access sheath assembly as in claim 1, wherein the third member comprising a groove along a length of the third member, wherein at least part of the second member is configured to be disposed in the groove when in the first configuration.

3. A medical access sheath assembly as in claim 2 where the second member comprises a foil, where the foil is substantially folded in the groove as the first configuration, and where the foil is substantially unfolded as the second configuration when the third member is removed from the channel.

4. A medical access sheath assembly as in claim 1 where the first member comprises a shape memory material, and where the second member comprises a polymer material.

5. A medical access sheath assembly as in claim 1 where the medical access sheath assembly has an expanded configuration with the channel having the second cross-sectional size, where the medical access sheath assembly is configured to automatically expand from a collapsed configuration, with the channel having the first cross-sectional size, to the expanded configuration with the channel having the second cross-sectional size.

6. A medical access sheath assembly as in claim 1 where the first member comprises a substantial semi-circular portion and two movable flap portions extending from opposite sides of the substantial semi-circular portion.

7. A medical apparatus comprising:
   a medical access sheath comprising:
      a first member comprising a length with a channel therethrough, where the first member comprises a wall having a gap through the wall, where the channel is configured to expand from a first cross-sectional size to a larger second cross-sectional size, and where the gap is configured to enlarge as the channel expands; and
      a second member connected to the first member, where the second member extends across the gap, and where the second member is configured to expand from a first configuration to a second configuration; and
   a dilator located in the channel, where the dilator comprises a receiving area defined at least partially by a notch through a wall of the dilator, where the receiving area comprises a portion of the second member located therein, and where the receiving area is configured to release the second member from a collapsed first configuration to an expanded second configuration as the dilator is slid out of the medical access sheath.

8. An apparatus comprising:
   a medical access sheath dilator; and
   a medical access sheath connected to the medical access sheath dilator,
   where the medical access sheath dilator is configured to be inserted through a channel of the medical access sheath, where the dilator comprises a receiving area defined at least partially by a notch through a wall of the dilator, where the receiving area is configured to have an expandable portion of the medical access sheath located therein, where the receiving area is configured to release the expandable portion from a first collapsed configuration to an expanded second configuration as the dilator is slid out of the medical access sheath.

9. An apparatus as in claim 8 where the medical access sheath comprises a first member comprising a channel therethrough, where the first member comprises a a wall having a gap through the wall, where the channel is configured to expand from a first cross-sectional size to a larger second cross-sectional size, and where the gap is configured to enlarge as the channel expands, and where the expandable portion is connected to the first member proximate the gap, where the expandable portion extends across the gap, and where the expandable portion is configured to expand when the channel expands from the first size to the second larger size.

* * * * *